United States Patent [19]

Abel

[11] Patent Number: 5,121,023

[45] Date of Patent: Jun. 9, 1992

[54] ULTRASONIC GENERATOR WITH A PIEZOELECTRIC CONVERTER

[75] Inventor: Martin Abel, Köln, Fed. Rep. of Germany

[73] Assignee: Ferton Holding, Delmont, Switzerland

[21] Appl. No.: 552,710

[22] Filed: Jul. 16, 1990

[51] Int. Cl.⁵ .............................. H01L 41/08
[52] U.S. Cl. .................... 310/316; 310/318
[58] Field of Search ................ 310/316, 318

[56] References Cited

U.S. PATENT DOCUMENTS

| | | | |
|---|---|---|---|
| 3,596,206 | 7/1971 | Loria | 331/116 |
| 4,748,365 | 5/1988 | Poupaert et al. | 310/316 |
| 4,868,445 | 9/1989 | Wand | 310/316 |
| 4,879,528 | 11/1989 | Gotanda | 310/316 |
| 4,901,034 | 2/1990 | Frank-Peter | 310/316 |
| 4,914,337 | 4/1990 | Takagi | 310/316 |
| 4,926,084 | 5/1990 | Furutsu et al. | 310/316 |
| 4,965,532 | 10/1990 | Sakurai | 310/316 |
| 4,966,131 | 10/1990 | Houghton et al. | 310/316 |

FOREIGN PATENT DOCUMENTS

| | | |
|---|---|---|
| 3641058C2 | 5/1989 | Fed. Rep. of Germany . |
| 25211B1 | 5/1981 | France . |
| 0268474 | 11/1988 | Japan ............ 310/318 |
| 0214276 | 8/1989 | Japan ............ 310/318 |
| 0026285 | 1/1990 | Japan ............ 310/318 |

Primary Examiner—Mark O. Budd
Assistant Examiner—Thomas M. Dougherty
Attorney, Agent, or Firm—Ratner & Prestia

[57] ABSTRACT

In an ultrasonic generator the driver circuit of a piezoelectric converter is provided with a switching regulator under control of a microcomputer, the pulse duty factor and frequency of the switching regulator being controlled in response to the converter's impedance which is detected by means of a measuring circuit.

8 Claims, 1 Drawing Sheet

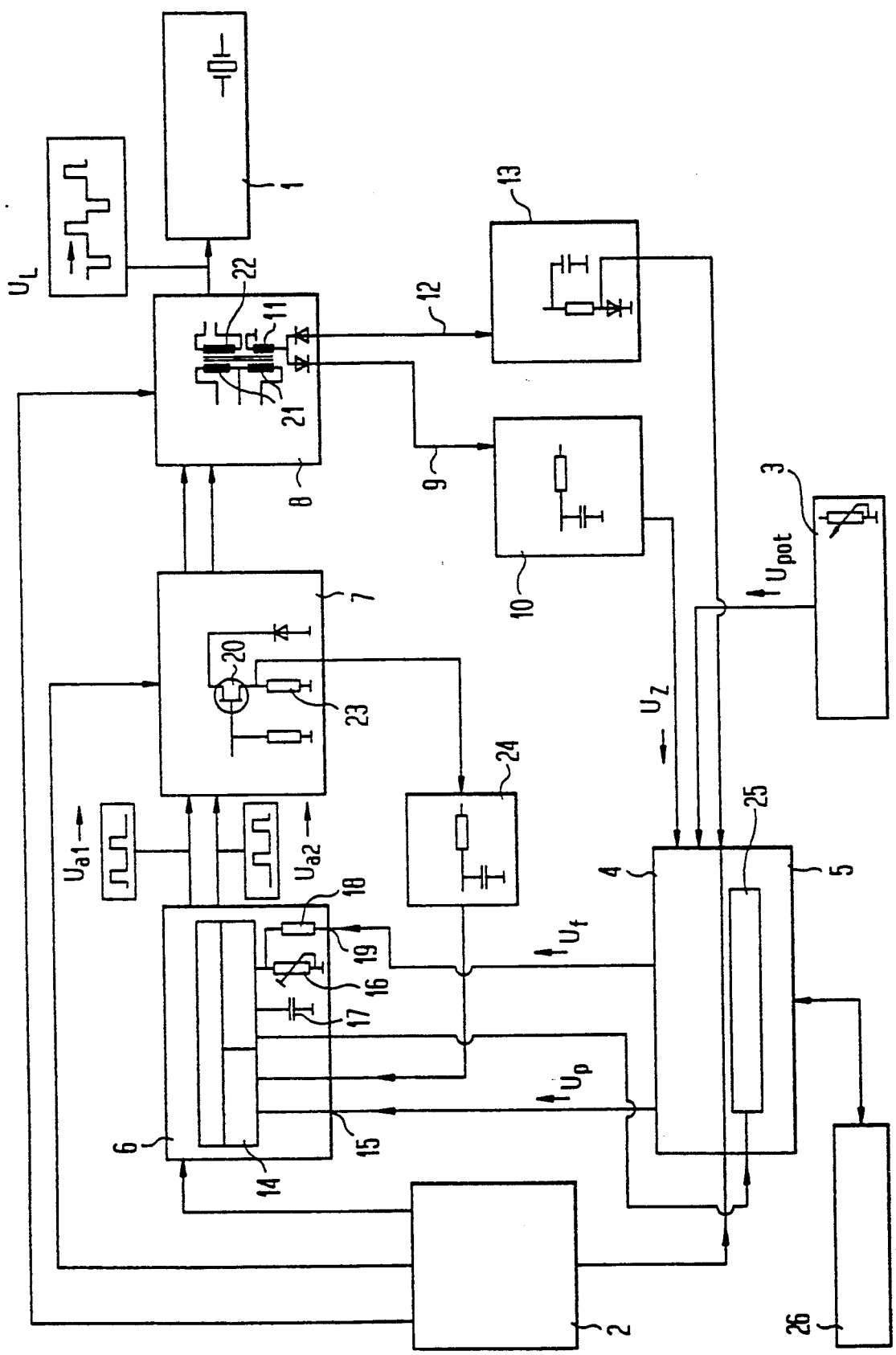

ULTRASONIC GENERATOR WITH A PIEZOELECTRIC CONVERTER

FIELD OF THE INVENTION

The present invention relates to an ultrasonic generator comprising a piezoelectric converter.

BACKGROUND OF THE INVENTION

In an ultrasonic generator known from the U.S. Pat. No. 3,596,206, an oscillator with a transistor of a self-oscillating design is known which is disposed in the driver circuit of a piezoelectric converter in combination with an amplifier and an impedance converter, both in series circuit array. For such an application, the transistor is connected in series to the primary winding of the impedance converter, i.e. a transformer, so as to constitute a modified Meissner circuit, and is set to its resonance working point by means of a voltage divider. The voltage divider includes a connection to a reaction coil which is inductively coupled to the primary winding of the transformer. In this way the transistor is given a frequency which equals the series resonance frequency of the piezoelectric converter in series with the secondary winding of the transformer. The driver circuit of the converter, or its series transformer, respectively, are moreover supplied from a power-pack through a rectifier connected to the primary side of the transformer and through a smoothing capacitor parallel thereto. The reaction coil of the transformer and the transistor are connected to each other through a series circuit including a capacitor and a resistor. That series circuit serves to match the reaction, which prevails between the piezoelectric converter and the transistor and which may be deactivated arbitrarily by means of an interrupter so as to achieve protection of the converter.

The French Patent FR-A-81 09 330 also discloses an ultrasonic generator designed to include a piezoelectric converter as well, wherein the circuit array includes not only a transistor providing a comparably self-oscillating oscillator but also a constant-current source provided with two further transistors and several resistors. In that circuit the potentiometer serves to trim the limiting current which is supplied to the converter when power acceptance is missing.

In the known ultrasonic generators with a piezoelectric converter, the self-oscillating design of the oscillator creates a direct dependence of the conditions of converter operation on the tolerances of the circuit elements directly connected thereto. Variations in the mutually matched tolerances of the components, which are mostly unavoidable in mass production based on devices obtained from different suppliers, create critical interfering effects on the oscillator's characteristics of oscillation and thus on the power output of the piezoelectric converter, too. The elimination of such interfering effects is possible only with a higher expenditure in terms of devices and costs.

The German Patent DE-A-36 41 058 discloses an ultrasonic generator with a magnetostrictive converter whose energizing coil is disposed in the collector circuit of a transistor. The emitter circuit of the transistor is connected through a resistor disposed to detect the current flow through the energizing coil and through a voltage evaluation circuit to control means causing the supply of the energizing pulses to the base of the transistor. The voltage evaluation circuit supplies a digital signal in response to the voltage drop at the resistor and is constituted either by a series circuit including a voltage frequency divider and a counter, or by a series circuit including a DC voltage suppression circuit, a low-pass circuit, and an A/D converter. The output of the control means is connected to a counter which emits pulses at a pulse rate determined by the signal supplied by the voltage evaluation circuit. The transmission of these pulses to the base of the transistor is determined by a timed switching regulator which is controlled by the control means. The control means is also connected to a potentiometer so as to provide for variation of the power output preset for the magnetostrictive converter.

In these known ultrasonic generators with a magnetostrictive converter the control means is only provided for setting of the pulse rate of the energizing pulses to the resonance working point of the converter. In these devices, during a primary trimming phase of the circuit array, pulses of a respectively predetermined number of pulse rates are supplied to the energizing coil in respectively successive smaller pulse rate ranges. Moreover, an uncomplex error indicator is provided as a monitor of each of the pulse rate ranges of the energizing pulse which are thus invariably set at individual trimming levels by the start of operation, at which the magnetostrictive converter operates at a resonance frequency, that monitor being under control of the control means such that any variation of that resonance frequency from the invariably set pulse rate range furnishes the mere indication of an error that has occurred, without correcting the actual source of the error at the same time.

The present invention refers to the problem of designing an ultrasonic generator with a piezoelectric converter in a way that the power output of the converter is less critically dependent on tolerances of the connected devices of the circuit array and that also an optimum possibility of correction of that power output is achieved when the set resonance working point of the converter should vary during operation of the ultrasonic generator.

SUMMARY OF THE INVENTION

In the inventive ultrasonic generator the oscillator is provided with a timed switching regulator whose pulse duty factor and frequency are controlled by a microcomputer. The microcomputer performs a permanent actual/reference comparison between the impedance detected by means of an impedance-measuring circuit for the piezoelectric converter, which is defined as actual value, and the preset power for its resonance working point, which may be varied by means of a potentiometer and serves as reference value, and in the event of any detected variation from the reference value it controls an adaptation of the pulse duty factor by means of a control voltage supplied to a control input of the switching regulator, and/or an adaptation of the frequency by means of a control voltage supplied to a control input of the switching regulator. The respective control inputs of the switching regulator, the impedance-measuring circuit and the potentiometer are connected to an input/output attachment circuit of the microcomputer.

With the oscillator being provided with a timed switching regulator and being combined with a microcomputer for control of its pulse duty factor and its frequency, it is possible now to allow for a very simple mutual matching and trimming of all the variable tolerances of the circuit which take an influence on the power output of the converter. The permanent actual/reference comparison made by the microcomputer moreover provides for a continuous consideration of any variation of the converter power output during operation of the ultrasonic generator, with the coherent variation of the impedance of the circuit system being linked up with a simple adaptive loop control of the switching regulator. The application of the microcomputer entails the additional substantial advantage that now the manufacturer of the equipment is able to schedule convertible individual programs with different preset power levels for the so implemented actual/reference comparison, such that a correspondingly universally applicable ultrasonic generator may be made available which allows the users to operate without any problems due to an individual program available and conceivable for any specific sequence of operations.

BRIEF DESCRIPTION OF THE DRAWING

The drawing illustrates a schematic block diagram of one embodiment of the inventive ultrasonic generator.

DETAILED DESCRIPTION OF THE INVENTION

The ultrasonic generator is provided with a piezoelectric converter 1 whose driver circuit is supplied with an operating voltage $U_L$ from a power-pack 2 operating on DC voltage. The power-pack 2 is provided with a rectifier and a smoothing capacitor. With application of the ultrasonic generator in a dental equipment the piezoelectric converter is located in a handheld part connected to the equipment through a connecting cable such that the ultrasound converted by means of the converter is applied for dental therapy at an instrument attachment specifically designed for tartar scaling from teeth or also for the treatment of the root of a tooth. In dental treatment applications thus different preset power levels are available for the so-called resonance working point of the converter, which may be selected for an adapted potential variation of its operating voltage $U_L$ by means of a potentiometer 3.

The tapping point of the potentiometer 3 is connected to the input/output attachment circuit 4 of a microcomputer 5 supplied from the power-pack 2. The microcomputer establishes a control means in feedback circuit with the piezoelectric converter 1, which controls a switching regulator 6 supplied in a tandem connexion from the power-pack 2, e.g. a regulator 6 of the TL 494 type available from Texas Instruments. The switching regulator 6 is connected to an impedance converter 8 through an amplifier 7, which are both supplied from the power-pack 2 with a supply voltage substantially higher than the voltage supplied to the microcomputer 5 and the switching regulator 6. The impedance converter 8 is made available by a transformer supplying the operating voltage $U_L$ for the piezoelectric converter 1.

The piezoelectric converter 1 is in feedback circuit with the microcomputer 5 through an impedance-measuring circuit 9 connected to the impedance converter 8. The impedance-measuring circuit 9 includes an integrator 10 in the form of a low-pass filter and is connected to an auxiliary coil 11 of the impedance converter 8. The magnetic coupling of the impedance converter 8 may be detected, in a correspondingly optimum way, for a correspondingly precise detection of the actual impedance value of the overall driver circuit of the piezoelectric converter 1. The impedance-measuring circuit 9 serves to supply to the microcomputer 5 a measured voltage $U_z$ value in correspondence to the so established actual impedance value so that a permanent actual/reference comparison may be carried out on the basis of this measured value. Moreover, the operating voltage for the input/output attachment circuit 4 of the microcomputer 5 is tapped at the auxiliary winding 11, with a voltage regulator 13 being disposed in the respective supply line 12.

The switching regulator 6, which is under control of the microcomputer 5, is provided on the secondary side of the mains transformer. The DC voltage supplied by means of the rectifier of the power-pack 2 is converted into an AC voltage by the switching regulator 6, whose pulse duty factor or duty cycle determines the operating voltage $U_L$ supplied to the amplifier 7. The pulse duty factor is determined by a control amplifier 14 which is provided at one control input 15 of the switching regulator 6 and connected to the input/output attachment circuit 4 of the microcomputer 5. The pulse duty factor may therefore be controlled by the microcomputer 5, with the decisive control voltage $U_P$ being obtained from the voltage $U_{pot}$ of the preset power which is converted as the reference for the working point of the piezoelectric converter 1. The frequency of the output voltage of the voltage regulator 6 is also obtained using a trimming resistor 16 and a capacitor 17 which are both connected to a control input 19 of the switching regulator 6 through a frequency-modulating series resistor 18. The control input 19, too, is connected to the input/output attachment circuit 4 of the microcomputer 5 such that the frequency of the output voltage may also be controlled by a control voltage $U_f$ ranging between 0 and 2.5 V such that it is maintained at a mean time value depending on the resonance working point of the converter.

The amplifier 7 is preferably provided with two transistors operating in the push-pull mode such that a limitation of its operating voltage $U_L$ to 300 V approximately will be obtained for the piezoelectric converter. The use of one transistor 20 only for the amplifier 7 would furnish an operating voltage in the range of 600 V so that this push-pull stage serves to improve the driving characteristics and mainly to provide for depolarization protection for the piezoelectric converter. Field-effect transistors are the preferred transistors which are supplied with the timed output voltages $U_{a1}$ and $U_{a2}$ in alternation from the switching regulator 6. Following amplification in the amplifier 7, the timed output voltages of the switching regulator 6 are supplied to two primary coils 21 of the impedance converter 8 whose secondary coil 22 transforms them into the operating voltages $U_L$. The amplification of the output voltage from the switching regulator 6 may be even more refined by the provision that the amplifier current is tapped at a grounded resistor 23 and is supplied through an integrator 24 of a low-pass configuration via the control input 15 of the switching regulator 6 to the control amplifier 14. In this manner a feedback loop is achieved for control of the pulse duty factor of the switching regulator 6, which is used to maintain the amplifier current at a constant level. This feedback provision is even more refined by a connection of the switching regulator 6 to a frequency counter 25 of the microcomputer 5 so that in this way all potentials of the circuit system are utilized for an optimum determination and also a permanent monitoring of the resonance working point of the piezoelectric converter 1.

The mode of operation of the aforedescribed ultrasonic generator applied in an equipment for ultrasonic dental treatment is thus substantially based on the following facts and conditions. Following the start of operation of the equipment initially the microcomputer 5 updates a frequency-impedance analysis for the piezoelectric converter 1 integrated into the hand-held operating element, which analysis depends on the power level preset by means of the potentiometer 3. To this end, using the microcomputer 5, the impedance detected by the impedance-measuring circuit 9 at the auxiliary winding 11 of the impedance converter 8 is determined as an absolute value of the corresponding voltage $U_Z$ which thus influences the resonance working point of the piezoelectric converter 1 or its series resonance frequency, respectively. This determination entails the detection of a reference value for the control voltage $U_f$ which sets the operating voltage $U_L$ of the piezoelectric converter 1. With a given resonance working point of the piezoelectric converter 1 its operating voltage $U_L$, on the other hand, occurs at a frequency at which the steady state impedance characteristic of a typical piezoelectric converter shows a sudden drop to a low value which, however, is again left immediately when the frequency determining the resonance working point of the converter is exceeded. With that primary determination of the reference value of the control voltage $U_f$ and thus of a predetermined resonance working point of the piezoelectric converter 1 also the amplifier current is considered due to the feedback which is established through the resistor 23 and the integrator 24 to the control amplifier 14 of the switching regulator 6, as well as by the further feedback to the frequency counter 25 of the microcomputer 5.

As soon as the operator uses the hand-held part of the equipment the impedance-measuring circuit 9 provides a permanent feedback to the microcomputer 5 in order to cause an actual/reference comparison against the preset power level previously selected at the potentiometer 3. Any variation established in such a permanent comparison causes control adjustment of the switching regulator 6, either at the control input 15 for adaptation of the pulse duty factor or/and at the control input 19 for adaptation of the operating voltage $U_L$ of the piezoelectric converter 1.

The integration of the microcomputer 5 for controlling the switching regulator 6 also provides the opportunity of connecting an external peripheral device 26 to an interface of the microcomputer, such as a personal computer for servicing and maintenance purposes. It may also be used to render an operating program available for the ultrasonic generator, which considers the different preset power levels, e.g. for tartar scaling from teeth which may be carried out by means of the hand-held part, on the one hand, and a treatment of the root of a tooth, on the other hand, which may be carried out using a replaced instrument attachment of the hand-held part. With such a configuration, the consideration is supported by empirical values for achievement of a respectively optimum dental treatment using the different instrument attachments coming into question so that the operation of this equipment no longer requires the experimental operation on the basis of individually preset power levels.

The switching regulator 6, which is timed in secondary circuit and is implemented as a step-up converter in cooperation with the transformer, may also be substituted by a primary-timed switching regulator. In such a case a high-frequency transformer ought to be used for isolation from the mains, rather than the normal mains transformer. Moreover, in an alternative embodiment the impedance-measuring circuit connected to the auxiliary winding 11 of the impedance converter 8 may also include a connection to the primary coil 21 or even the secondary coil 22 of the impedance converter. If provisions are made for measurement of the amplifier current in another alternative it is finally also possible to provide a measuring circuit which is connected to the output side of the integrator 24 rather than to the impedance converter 8.

What is claimed is:

1. An ultrasonic generator comprising:
   a) a piezoelectric converter having a power output and a driver circuit, said driver circuit comprising an amplifier supplying a signal to said piezoelectric converter through an oscillator;
   b) an impedance converter connected in series with said oscillator;
   c) an impedance measuring circuit for said piezoelectric converter connected in series with said oscillator, said impedance measuring circuit measuring actual impedance;
   d) a microcomputer having a reference value, said reference value related to a permanent frequency of said power output of said piezoelectric converter, wherein said microcomputer performs a permanent comparison between said reference value and said actual impedance;
   e) means for setting said reference value; and
   f) a timed switching regulator connected to said amplifier, said timed switching regulator producing a pulse duty factor and a frequency, at least one of said pulse duty factor and said frequency under the control of said microcomputer in accordance with any variations of said actual impedance with respect to said reference value.

2. An ultrasonic generator according to claim 1, wherein said amplifier operates on a constant current and wherein said constant current is tapped through a grounded resistor of said amplifier and supplied to a control input of said timed switching regulator through an integrator implemented as a low-pass device.

3. An ultrasonic generator according to claim 2 further comprising a frequency counter of said microcomputer, wherein said timed switching regulator is connected in a feedback loop to said frequency counter of said microcomputer.

4. An ultrasonic generator according to claim 1 further comprising an interface of said microcomputer, wherein an external peripheral equipment is connected to said interface of said microcomputer.

5. An ultrasonic generator according to claim 4, wherein said peripheral equipment connected to said interface of said microcomputer is a personal computer for servicing and maintenance.

6. An ultrasonic generator according to claim 1 wherein said microcomputer is provided with an operating program considering different resonance working points of said piezoelectric converter at different preset power levels, and adapted for changeover between the various individual programs corresponding respectively to a specific preset power level.

7. An ultrasonic generator according to claim 1 further comprising an auxiliary coil of said impedance converter, wherein said impedance-measuring circuit is connected to said auxiliary coil of said impedance converter.

8. An ultrasonic generator according to claim 1, wherein said amplifier is provided with two transistors operating in push-pull mode.

* * * * *

UNITED STATES PATENT AND TRADEMARK OFFICE
CERTIFICATE OF CORRECTION

PATENT NO. : 5,121,023
DATED : June 9, 1992
INVENTOR(S) : Martin Abel

It is certified that error appears in the above—identified patent and that said Letters Patent is hereby corrected as shown below:

Title page, after "[22]  Filed: Jul. 16, 1990", insert the following lines:

--[30]      Foreign Application Priority Data
        Aug. 1, 1989 [DE] Germany...... P 39 25 459.3--.

Signed and Sealed this

Third Day of August, 1993

Attest:

MICHAEL K. KIRK

Attesting Officer    Acting Commissioner of Patents and Trademarks